US009505679B2

United States Patent
Fritz et al.

(10) Patent No.: US 9,505,679 B2
(45) Date of Patent: Nov. 29, 2016

(54) PROCESS FOR PREPARING OLEFINS BY THERMAL STEAMCRACKING IN CRACKING FURNACES

(71) Applicant: Linde Aktiengesellschaft, Munich (DE)

(72) Inventors: Helmut Fritz, Munich (DE); Stefanie Walter, Seehausen (DE); Gunther Schmidt, Deisenhofen (DE)

(73) Assignee: Linde Aktiengesellschaft, Munich (DE)

( * ) Notice: Subject to any disclaimer, the term of this patent is extended or adjusted under 35 U.S.C. 154(b) by 102 days.

(21) Appl. No.: 14/420,630

(22) PCT Filed: Aug. 6, 2013

(86) PCT No.: PCT/EP2013/002347
§ 371 (c)(1),
(2) Date: Feb. 9, 2015

(87) PCT Pub. No.: WO2014/023417
PCT Pub. Date: Feb. 13, 2014

(65) Prior Publication Data
US 2015/0218065 A1 Aug. 6, 2015

(30) Foreign Application Priority Data
Aug. 9, 2012 (EP) .................................... 12005782

(51) Int. Cl.
*C07C 4/04* (2006.01)
*C10G 9/36* (2006.01)

(52) U.S. Cl.
CPC . *C07C 4/04* (2013.01); *C10G 9/36* (2013.01); *C10G 2400/20* (2013.01)

(58) Field of Classification Search
None
See application file for complete search history.

(56) References Cited

U.S. PATENT DOCUMENTS

| | | | |
|---|---|---|---|
| 2,017,874 A | 10/1935 | Sullivan | |
| 6,743,961 B2 | 6/2004 | Power | |
| 7,268,265 B1 * | 9/2007 | Stewart | C07C 4/06 585/313 |

(Continued)

FOREIGN PATENT DOCUMENTS

| | | |
|---|---|---|
| CN | 1665911 A | 9/2005 |
| CN | 101092325 A | 12/2007 |

OTHER PUBLICATIONS

PCT/EP2013/002347 English Translation of the International Preliminary Report on Patentability Chapter II, mailed Nov. 13, 2014, 7 pages.

(Continued)

*Primary Examiner* — Tam M Nguyen
(74) *Attorney, Agent, or Firm* — Lathrop & Gage LLP

(57) ABSTRACT

The invention relates to a process for converting hydrocarbon feeds by thermal steamcracking to at least one olefin-containing product stream comprising at least ethylene and propylene, with at least partial conversion of a first hydrocarbon feed in at least one first cracking furnace (1) and of a second hydrocarbon feed in at least one second cracking furnace (2). According to the invention, the second hydrocarbon feed is converted in the second cracking furnace (2) with cracking conditions that lead to a ratio of propylene to ethylene of 0.7 to 1.6 kg/kg, and the first hydrocarbon feed is converted in the first cracking furnace (1) with cracking conditions that lead to a ratio of propylene to ethylene of 0.25 to 0.85 kg/kg at the cracking furnace exit, the value for the ratio of propylene to ethylene for the second hydrocarbon feed being above the value for the ratio of propylene to ethylene for the first hydrocarbon feed.

14 Claims, 2 Drawing Sheets

(56) References Cited

U.S. PATENT DOCUMENTS

| | | |
|---|---|---|
| 8,178,060 B2 * | 5/2012 | Corradi .................. B01D 3/14 422/129 |
| 2004/0209964 A1 | 10/2004 | Ansorge et al. |
| 2008/0194900 A1 | 8/2008 | Bhirud |
| 2008/0223754 A1 | 9/2008 | Subramanian et al. |
| 2016/0168045 A1 * | 6/2016 | Schoenfeldt .............. C07C 1/20 585/324 |
| 2016/0168051 A1 * | 6/2016 | Palmas .................. C07C 4/06 585/635 |

OTHER PUBLICATIONS

PCT/EP2013/002347 English Translation of the International Search Report Nov. 13, 2014, mailed Oct. 23, 2013, 3 pages.

* cited by examiner

PROCESS FOR PREPARING OLEFINS BY THERMAL STEAMCRACKING IN CRACKING FURNACES

The present invention relates to a process for converting hydrocarbon feeds by thermal steamcracking to at least one olefin-containing product stream comprising at least ethylene and propylene, with at least partial conversion of a first hydrocarbon feed in at least one first cracking furnace and of a second hydrocarbon feed in at least one second cracking furnace.

Thermal steamcracking is a long-established petrochemical process. The standard target compound in thermal steamcracking is ethylene (also ethene), which is an important starting compound for a number of chemical syntheses.

The feeds used for the thermal steamcracking may be either gases such as ethane, propane or butane and corresponding mixtures or liquid hydrocarbons, for example naphtha, and hydrocarbon mixtures.

With regard to the specific apparatuses and reaction conditions used in thermal steamcracking, and with regard to the reactions which proceed and to details of refinery technology, reference is made to corresponding articles in reference works such as Zimmermann, H. and Walzl, R.: Ethylene, in: Ullmann's Encyclopedia of Industrial Chemistry, 6th ed. Weinheim: Wiley-VCH, 2005, and Mon, W. W. and Neuwirth, O. S.: Oil Refining, in: Ullmann's Encyclopedia of Industrial Chemistry. 6th ed. Weinheim: Wiley-VCH 2005. Processes for preparing olefins are also disclosed, for example, in U.S. Pat. No. 3,714,282 A and U.S. Pat. No. 6,743,961 B1, which includes a process for preparing olefins in which heavy oil is pretreated in a mild cracking process before it is conducted into a furnace for thermal cracking.

In addition, mention should be made here of US 2004/209964, which discloses that hydrocarbons which have a carbon number between 15 and 30 and have been produced by a Fischer-Tropsch synthesis and fractionated are hydrogenated and then thermally cracked under mild conditions.

For thermal steamcracking, cracking furnaces are used. The cracking furnaces, together with a quench unit and downstream devices for processing of the product mixtures formed, are integrated into corresponding larger plants for olefin production, which are referred to in the context of this application as "steamcrackers".

An important parameter in thermal steamcracking is the cracking severity, which determines the cracking conditions. The cracking conditions are influenced especially by the temperature and residence time and the partial pressures of the hydrocarbons and of the steam. The composition of the hydrocarbon mixtures used as the feed and the design of the cracking furnaces used also influence the cracking conditions. Because of the mutual influences of these factors, the cracking conditions are normally defined via the ratio of propylene (also referred to as propene) to ethylene in the cracking gas.

According to the feed mixture and cracking conditions, thermal steamcracking gives rise not only to ethylene, the standard target compound, but also to sometimes considerable amounts of by-products, which can be separated from a corresponding product stream. These include lower alkenes, for example propylene and butenes, and also dienes, for example butadienes, and also aromatics, for example benzene, toluene and xylenes. These are of comparatively high economic value, and so the formation thereof as "high-value products" is desirable.

The problem addressed by the present invention is therefore that of improving the means of obtaining olefin-containing product mixtures from hydrocarbons by thermal steamcracking.

DISCLOSURE OF THE INVENTION

Against this background, the invention proposes a process for converting hydrocarbon feeds by thermal steamcracking to at least one olefin-containing product stream comprising at least ethylene and propylene, with at least partial conversion of a first hydrocarbon feed in at least one first cracking furnace and of a second hydrocarbon feed in at least one second cracking furnace, having the features of the independent claims. Preferred configurations are the subject of the dependent claims and of the description which follows.

Advantages of the Invention

According to the invention, a process is proposed in which the second hydrocarbon feed is converted in the second cracking furnace with cracking conditions that lead to a ratio of propylene to ethylene of 0.7 to 1.6 kg/kg, and the first hydrocarbon feed is converted in the first cracking furnace with cracking conditions that lead to a ratio of propylene to ethylene of 0.25 to 0.85 kg/kg at the cracking furnace exit, the value for the ratio of propylene to ethylene for the second hydrocarbon feed being above the value for the ratio of propylene to ethylene for the first hydrocarbon feed. These first and second hydrocarbon feeds differ in terms of composition.

In the context of the invention, the first and second hydrocarbon feeds refer to all hydrocarbons which are conducted into the first and second cracking furnaces respectively. Thus, a first hydrocarbon feed is at least partly converted in a first cracking furnace and a second hydrocarbon feed in a second cracking furnace, each under cracking conditions as specified in claim 1. Cracking conditions as exist in the second cracking furnace and as specified in claim 1 with the corresponding ratio of propylene to ethylene are referred to hereinafter as mild cracking conditions, whereas cracking conditions as exist in the first cracking furnace and which are likewise specified in claim 1 by the ratio of propylene to ethylene are referred to hereinafter as normal cracking conditions. Normal cracking conditions are cracking conditions as typically used in thermal steamcracking.

A cracking furnace is understood in the context of this invention to mean a cracking unit in which the cracking conditions are defined. It is possible that a subdivision into two or more cracking furnaces is present in one overall furnace. In that case, reference is frequently made to furnace cells. A plurality of furnace cells forming part of an overall furnace generally have independent radiation zones and a common convection zone, and also a common smoke outlet. In these cases, each furnace cell can be operated with its own cracking conditions. Each furnace cell is thus a cracking unit and is consequently referred to here as a cracking furnace. In that case, the overall furnace has a plurality of cracking units or, in other words, it has a plurality of cracking furnaces. If only one furnace cell is present, this is the cracking unit and hence the cracking furnace. Cracking furnaces can be combined to form groups, which are supplied, for example, with the same feed. The cracking conditions within a furnace group are generally adjusted to be the same or similar.

The thermal cracking of hydrocarbons of typical composition, for example naphtha, under mild cracking conditions gives rise to very large amounts of pyrolysis gasoline, which is very difficult to deal with because of the large amount. This is a result of the comparatively lower conversion of the feed in the cracking furnace under mild cracking conditions. Mild cracking conditions, however, are desirable since a greater ratio of propylene to ethylene is present in the case of cracking under mild conditions than in the case of cracking under normal cracking conditions as typically used.

The process according to the invention makes it possible to operate the second cracking furnace under mild cracking conditions, since the feed and cracking conditions are matched to one another. Only through the matching of feed and cracking conditions is it possible to avoid the disadvantages described in the previous paragraph. These disadvantages and the solution indicated have been recognized in the context of the invention.

The process according to the invention thus makes it possible to operate a steamcracking plant in such a way that more propylene is formed in relation to the fresh feed than in a conventional plant in which the process according to the invention is not used.

The higher the ratio of propylene to ethylene selected for the cracking conditions in the second cracking furnace, the more propylene is formed in relation to the fresh feed. This is advantageous in the context of the invention. However, a higher ratio of propylene to ethylene is associated with a lower conversion of the feed, and so the values are subject to upper technical and economic limits. Within the limits specified in the claims, it is guaranteed that, on the one hand, the inventive advantages will be achieved and, on the other hand, the steamcracker will be controllable in an industrial context and operable in an economically viable manner.

Within the limits specified for the cracking conditions in the first cracking furnace, industrially and economically advantageous steamcracking is possible, which forms ethylene and propylene as primary products of value.

Advantageously, the second hydrocarbon feed is converted in the second cracking furnace with cracking conditions that lead to a ratio of propylene to ethylene of 0.8 to 1.4 kg/kg, more preferably of 0.85 to 1.2 kg/kg, at the cracking furnace exit.

Advantageously, the first hydrocarbon feed is converted in the first cracking furnace with cracking conditions that lead to a ratio of propylene to ethylene of 0.3 to 0.75 kg/kg, more preferably of 0.4 to 0.65 kg/kg, at the cracking furnace exit.

More particularly, the values for the ratio of propylene to ethylene for the first and second hydrocarbons differ by at least 0.1 kg/kg, preferably by at least 0.15 kg/kg, more preferably by at least 0.2 kg/kg, for the advantages of the invention to be achieved to a particular degree.

Advantageously, the second hydrocarbon feed comprises predominantly hydrocarbons having a maximum carbon number of 5. Such a hydrocarbon feed is particularly suitable for cracking under mild conditions. This is true to a very particular degree when the second hydrocarbon feed consists for the most part of hydrocarbons having a carbon number of 5 or/and 4.

The word "predominantly" is used in the context of this application to make it clear that the feed or the fraction does not consist exclusively of hydrocarbons having the specified carbon number, but that hydrocarbons having other carbon numbers and other impurities may also be present alongside the hydrocarbons of the specified carbon number. The separation and processing of the fresh feed, of the product stream and/or the fractions always leaves residues of the component(s) in the product stream or in the fraction. Other impurities also persist, and so a processed product stream or fraction stream always contains residues. Since the cost and inconvenience associated with separation and processing rise to an extremely high degree with the purity to be achieved, economic factors decide what proportion of residues may be present in a stream. The level of this proportion has to be weighed up according to economic considerations. A rough guide value for the proportion of unwanted hydrocarbons and other impurities will generally be that not more than 30 to 40 percent by weight may be present in the product stream and/or in the fraction. Usually, a maximum value of 15 percent by weight or less is actually attained. The hydrocarbon feed therefore contains the desired hydrocarbons at at least 60 percent by weight, preferably at least 80 percent by weight and further preferably at least 90 percent by weight and more preferably at least 95 percent by weight and most preferably at least 98 percent by weight. This applies to the fresh feed, to feed obtained from the fresh feed fractionation, and to feed from recycled components.

In a particularly advantageous configuration of the invention, the second cracking furnace is supplied with one or more recycled fractions which are obtained from the product stream and which comprise predominantly hydrocarbons having a carbon number of not more than 5. The second hydrocarbon feed thus comprises recycled fractions. Recycling of such fractions increases the amount of suitable feed for the second cracking furnace, or such a fraction constitutes a suitable second hydrocarbon feed for the second cracking furnace. A fraction comprising hydrocarbons having a carbon number of 4 and a fraction having a carbon number of 5 are also obtained in the processing of the product stream in steamcrackers, and these, after separation of the products of value, can be recycled directly or after further treatment steps.

In addition, it is advantageous to supply the first cracking furnace with at least one fraction which has been separated from the product stream and recycled, and which comprises predominantly hydrocarbons having a carbon number of at least 6. Such a fraction is suitable as the first hydrocarbon feed for the first cracking furnace.

Particularly advantageously, a fresh feed is used, which is fractionated into at least one first and one second fresh feed fraction, and the first fresh feed fraction is conducted at least partly into the first cracking furnace and the second fresh feed fraction at least partly into the second cracking furnace. A fractionation of the fresh feed can achieve the effect that, particularly for the second cracking furnace, a feed is available which can achieve the advantages of the invention in an outstanding manner. These first and second fresh feed fractions have a different composition. It is thus emphasized that the division of the fresh feed is a fractionation and not a simple division into two amounts. In a fractionation, a separation is effected according to different components. After the fractionation, some components of the fresh feed are thus present predominantly in the first fresh feed fraction, and other components of the fresh feed are present predominantly in the second fresh feed fraction.

In a further advantageous configuration of the invention, the second cracking furnace is supplied with a fresh feed consisting predominantly of hydrocarbons having a maximum carbon number of 5. Such a fresh feed can be obtained, for example, in a refinery or in natural gas production. Because of its characteristics, it is of very good suitability as a feed in the second cracking furnace under mild cracking conditions.

It should be emphasized once again here that the aforementioned feeds (recycled fractions, fresh feed fraction and fresh feeds composed of hydrocarbons having a maximum carbon number of 5) are suitable as feeds for the second cracking furnace, since all of them are outstandingly suitable for mild cracking. In order to gain the advantages of the invention, the feeds proposed here can be conducted individually or as a mixture into the second cracking furnace. The second hydrocarbon feed used may thus be one or more recycled fractions or a fresh feed fraction or another feed composed of hydrocarbons having a maximum carbon number of 5. It is also possible to use recycled fraction(s) and a fresh feed fraction or recycled fraction(s) and another feed composed of hydrocarbons having a maximum carbon number of 5 or a fresh feed fraction and another feed composed of hydrocarbons having a maximum carbon number of 5 or a mixture of all the possible feeds as the second hydrocarbon feed.

As explained at the outset, the ratio of propylene to ethylene in the thermal steamcracking operation results from a number of different influencing factors, among which the cracking furnace exit temperature, i.e. the temperature of a product stream on departure from the reactor coil used (coil output temperature), plays an important role. The cracking furnace exit temperature for the conversion in the second cracking furnace is advantageously between 680° C. and 820° C., preferably between 700° C. and 800° C. and further preferably between 710° C. and 780° C. and more preferably between 720° C. and 760° C., while the cracking furnace exit temperature for the conversion in the first cracking furnace is advantageously between 800° C. and 1000° C., preferably between 820° C. and 950° C. and more preferably between 840° C. and 900° C. The cracking furnace exit temperature in the first cracking furnace is always higher than in the second cracking furnace.

The cracking furnace exit temperature for the conversion in the first cracking furnace is preferably at least 10° C. above, more preferably at least 15° C. above and most preferably at least 20° C. above, the cracking furnace exit temperature for the conversion in the second cracking furnace.

In the second cracking furnace, a lower steam dilution than in the first can also be used. This reduces the amount of dilution steam needed and saves energy. However, a lower steam dilution in the second cracking furnace is unnecessary for the significant advantages of the invention to be manifested. Advantageously, in the second cracking furnace 0.15 to 0.8 kg of steam per kg of hydrocarbon is used in the feed, whereas in the first cracking furnace 0.3 to 1.5 kg of steam per kg of hydrocarbon is used in the feed.

It is also advantageously possible to convert especially saturated hydrocarbons having a carbon number of 2 to 3 present in the product stream by means of thermal steamcracking in a cracking furnace for gaseous feed. To this end, the saturated gaseous hydrocarbons are obtained from the product stream, and recycled into and converted in the cracking furnace for gaseous feed.

The fresh feeds used for the first hydrocarbon feed or/and the fresh feeds used for fresh feed fractionation may be either gases or gas fractions, such as ethane, propane or butane, and corresponding mixtures and condensates, or liquid hydrocarbons and hydrocarbon mixtures. These gas mixtures and condensates comprise especially what are called natural gas condensates (natural gas liquids, NGL). The liquid hydrocarbons and hydrocarbon mixtures may originate, for example, from what is called the gasoline fraction of crude oil. Such crude gasolines or naphthas (NT) and kerosene are mixtures of preferably saturated compounds having boiling points between 35 and 210° C. However, the invention is also advantageous in the case of use of middle distillates, atmospheric residues and/or mixtures derived therefrom from crude oil processing. Middle distillates comprise what are called light and heavy gas oils which can be used as starting materials for production of light heating and diesel oils and of heavy heating oil. The compounds present have boiling points of 180 to 360° C. They are preferably predominantly saturated compounds which can be converted in a thermal steamcracking operation. In addition, it is also possible to use fractions obtained by known distillative separation processes and corresponding residues, but also the use of fractions derived therefrom, for example by hydrogenation (hydrotreating) or hydrocracking. Examples are light, heavy and vacuum gas oil (atmospheric gas oil, AGO, or vacuum gas oil, VGO), and also mixtures and/or residues treated by the hydrogenation processes mentioned (hydrotreated vacuum gas oil, HVGO, hydrocracker residue, HCR, or unconverted oil, UCO).

Very particularly advantageous fresh feeds for the first hydrocarbon feed are liquid hydrocarbons. More particularly, the fresh feeds used are natural gas condensates and/or crude oil fractions and/or mixtures derived therefrom.

Advantageously, the invention thus encompasses the use of hydrocarbon mixtures having a boiling range of up to 600° C. as the first hydrocarbon feed as fresh feed for the first hydrocarbon feed. Within this overall range, it is also possible to use hydrocarbon mixtures having different boiling ranges, for example having boiling ranges of up to 360° C. or of up to 240° C. The reaction conditions in the cracking furnace are matched here to the hydrocarbon mixtures used in each case.

For instance, the invention can, however, also be used advantageously with any desired fresh feeds having comparable properties, for example biogenic or/and synthetic hydrocarbons.

BRIEF DESCRIPTION OF THE DRAWING

The process according to the invention in a particularly advantageous configuration is to be elucidated in detail with reference to the process flow diagrams which show the essential process steps in schematic form. For better understanding, the known process is first illustrated with reference to FIG. 1.

Figure 1:
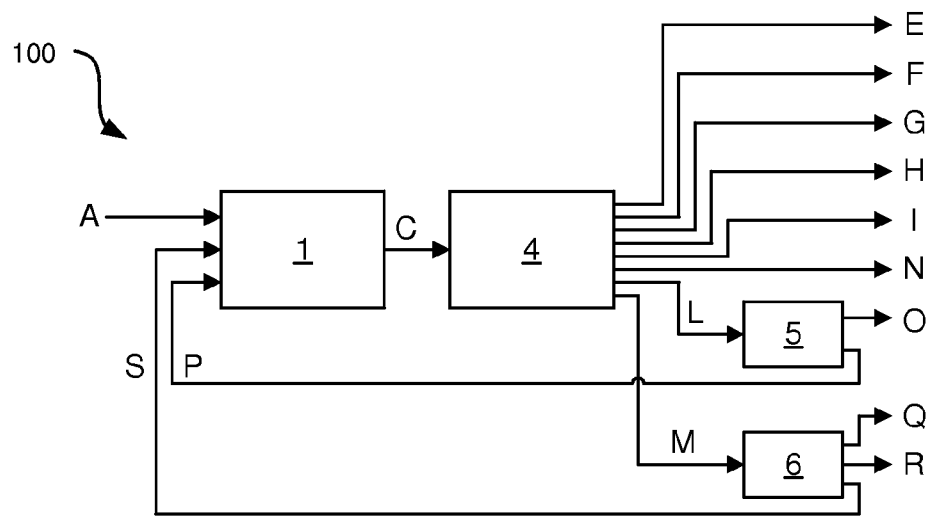
FIG. 1 shows to this end a schematic view of a known method for olefin production.

The schematic process flow diagram 100 of FIG. 1 for the known process includes a cracking furnace 1 into which the fresh feed A (for example naphtha) and the recycled fractions S and P as hydrocarbon feeds are conducted. In the cracking furnace 1, the hydrocarbon feed is heated and converted in convection and radiation zones. Steam is added to the cracking furnace, usually 0.5 to 1 kg of process steam per kg of hydrocarbon. A product stream C emerges from the cracking furnace 1, and this is also referred to as the cracking product stream directly at the exit from the cracking furnace. On exit from the cracking furnace, this cracking product stream has a temperature normally between 840° C. and 900° C. The ratio of propylene to ethylene is generally 0.35 to 0.6 kg/kg. After a first quench (not shown), the product stream is processed in a processing unit 4. From the processing unit, the following fractions are obtained as essential product fractions E to N: hydrogen E, waste liquor F, methane G, ethylene H, propylene I, gaseous hydrocarbons L having a carbon number of 4, pyrolysis gasoline M and pyrolysis oil N. The gaseous hydrocarbons L having a carbon number of 4 are treated further in a C4 processing unit 5, which is utilized for the processing of hydrocarbons having a carbon number of 4. Such a C4 processing unit 5 treats the fraction having a carbon number of 4 further in such a way that butadiene O can be removed. The other hydrocarbons having a carbon number of 4 constitute a fraction P which is recycled into the cracking furnace 1. The pyrolysis gasoline M comprising hydrocarbons having a carbon number of 5 or more is processed further in a pyrolysis gasoline processing unit 6, and aromatics Q and hydrocarbons R having a carbon number of, for example, more than 9 are removed. The other hydrocarbons having a carbon number of 5 or more are recycled as fraction S into the cracking furnace 1. The processing unit 4, and also the C4 processing unit 5 and the pyrolysis gasoline processing unit 6, comprise customary units for further processing of the product stream or of the product fractions, which serve to execute various process steps, for example compression, condensation and cooling, drying, distillation and fractionation, extraction and hydrogenation. The process steps are customary in olefin plants are are known to those skilled in the art.

Figure 2:
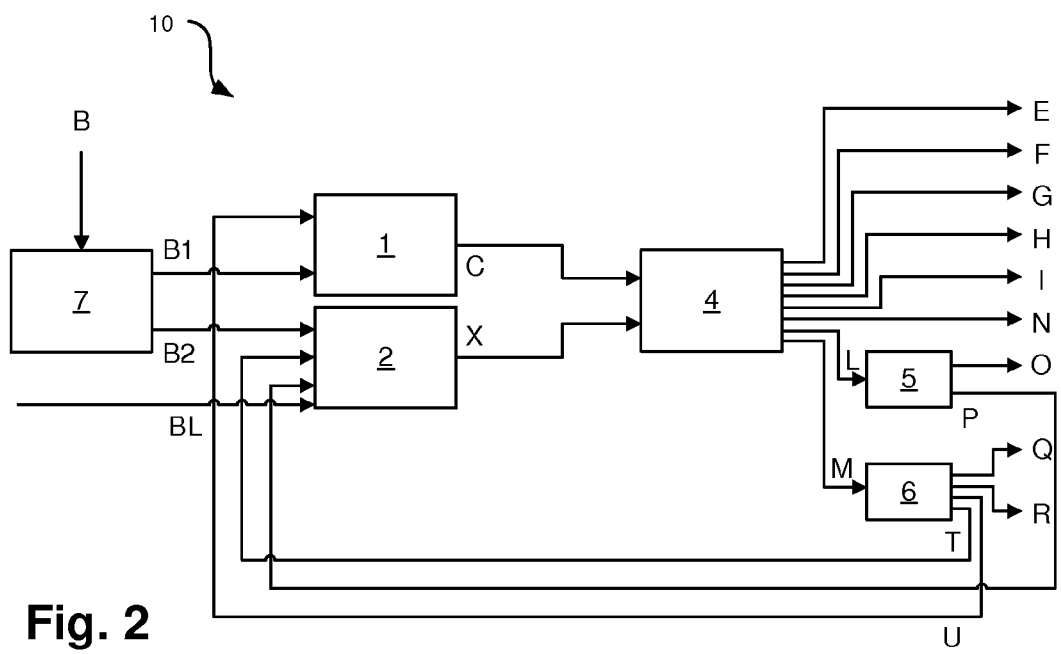
FIG. 2 shows a schematic view of the essential steps of the process according to the invention in a particularly advantageous configuration.

The schematic process flow diagram 10 of FIG. 2 then shows the process according to the invention in a particularly advantageous configuration, and the essential process steps thereof. In addition to the cracking furnace 1, a second cracking furnace 2 is present here, as is a fresh feed fractionation unit 7. A fresh feed B (for example naphtha) is then fractionated in the fresh feed fractionation unit 7 and the first fresh feed fraction B1 is conducted into the first cracking furnace 1, while the second fresh feed fraction B2 is conducted into the second cracking furnace 2. For the processes for fractionation of the fresh feed, the customary methods for separation and treatment of hydrocarbon streams are used, as known from olefin plants from refineries. The person skilled in the art knows of these, and how to use them. A fraction U is additionally recycled into the first cracking furnace 1, and the fractions T and P are additionally recycled into the second cracking furnace 2 (for further details see below). In addition, the second cracking furnace is supplied with a further feed BL composed of hydrocarbons having a maximum carbon number of 5 as a fresh feed. In turn, the cracking product stream C having the abovementioned properties emerges from the first cracking furnace 1. The cracking product stream X emerges from the second cracking furnace 2. The cracking product stream X is at a temperature advantageously between 700° C. and 800° C. The ratio of propylene to ethylene therein is advantageously between 0.7 and 1.5 kg/kg. The product streams C and X are processed further in the processing unit 4 and combined at a suitable point to give a common product stream. The processes for further treatment and processing in the processing unit 4 are known and have just been described. Thus, the processing unit 4 also leads, as just described, to the product fractions E to N. The product fractions L and M too, as just described, are treated further in the specific processing units 5 and 6. In contrast to the process described in FIG. 1, the fraction P comprising hydrocarbons having a carbon number of 4 is then advantageously also recycled not into the cracking furnace 1 but into the second cracking furnace 2. In the pyrolysis gasoline processing unit 6, as well as the abovementioned fractions Q and R, the fractions T and U are obtained. The fraction T comprising hydrocarbons having a carbon number of 5 is advantageously recycled into the second cracking furnace 2, while the fraction U comprising hydrocarbons having a carbon number of 6 or more, especially between 6 and 9, is advantageously recycled into the first cracking furnace 1. In FIG. 2, various feeds for the second cracking furnace are conducted. These then form the second hydrocarbon feed. It should be mentioned that the enumeration of the various feeds is not conclusive and, more particularly, that the feeds shown in FIG. 2 for the second cracking furnace (B2, BL, T and P) need not always all be conducted into the second cracking furnace 2; instead, it is sufficient in many cases to conduct some of the possible feeds into the second cracking furnace 2, for example a recycled fraction T composed of hydrocarbons having a carbon number of 5 and a fresh feed BL composed of hydrocarbons having a maximum carbon number of 5 or, for example, recycled fractions T and P comprising hydrocarbons having carbon numbers of 5 and 4 and LPG BL. In short, the following feeds into the second cracking furnace are possible: B2, BL, T, P, B2+BL, B2+T, B2+P, BL+T, BL+P, T+P, B2+BL+T, B2+BL+P, B2+P+T, BL+P+T or B2+BL+P+T.

Figure 3:
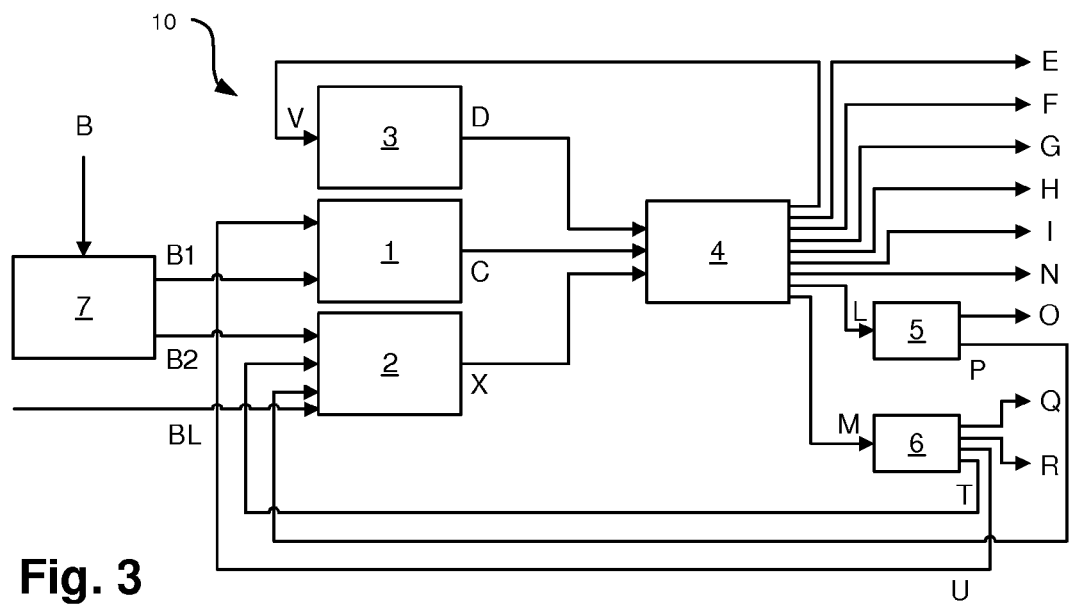
FIGS. 3 and 4 show, likewise in schematic form, the essential steps of a particularly advantageous configuration of the invention. In the figures, corresponding elements bear identical reference numerals.

A particularly advantageous configuration of the invention is likewise present in FIG. 3. FIG. 3 has the same schematic process flow diagram as also shown in FIG. 2. This is supplemented by a cracking furnace 3 for gaseous feed, into which a fraction V is conducted as feed. The fraction V comprises saturated gaseous hydrocarbons having a carbon number of 2 or 3, which are likewise obtained in the processing unit 4.

Figure 4:
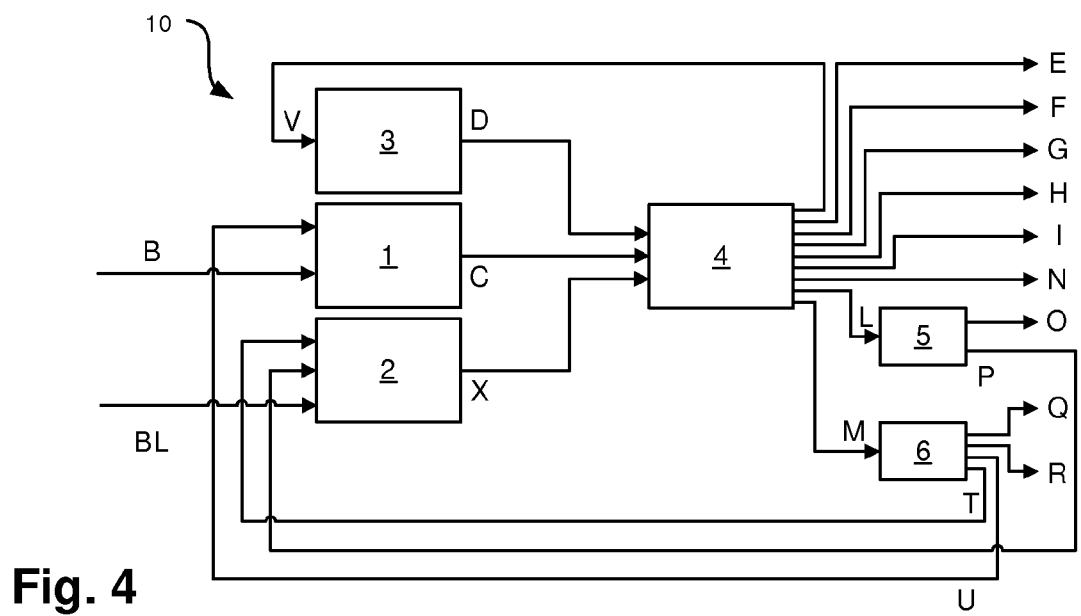

FIG. 4 too shows an advantageous configuration of the invention. FIG. 4 includes the same schematic process flow diagram as FIG. 2, except that the fresh feed fractionation is absent here. Fresh feed is added here as fresh feed B to the first cracking furnace 1, and a fresh feed BL composed of hydrocarbons having a maximum carbon number of 5 is added to the second cracking furnace 2. The further process steps have already been elucidated in the figure description for FIG. 2.

LIST OF REFERENCE NUMERALS

1 cracking furnace (normal cracking conditions)
2 cracking furnace (mild cracking conditions)
3 cracking furnace for gaseous feed
4 processing unit
5 C4 processing unit
6 pyrolysis gasoline processing unit
7 fresh feed fractionation unit
10 schematic process flow diagrams for a known process
100 schematic process flow diagrams for the process according to the invention in a particularly advantageous configuration
A, B, BL fresh feed
B1, B2 fresh feed fractions
C, D, X product streams
E-V product fractions

The invention claimed is:
1. A process for converting hydrocarbon feeds by thermal steamcracking to an olefin-containing product stream comprising at least ethylene and propylene, with at least partial conversion of a first hydrocarbon feed in at least one first cracking furnace (1) and of a second hydrocarbon feed in at least one second cracking furnace (2), characterized in that the second hydrocarbon feed is converted in the second cracking furnace (2) with cracking conditions that lead to a ratio of propylene to ethylene of 0.7 to 1.6 kg/kg at the cracking furnace outlet, and in that the first hydrocarbon feed is converted in the first cracking furnace (1) with cracking conditions that lead to a ratio of propylene to cethylene of 0.25 to 0.85 kg/kg at the cracking furnace exit, the value for the ratio of propylene to ethylene for the second hydrocarbon feed being above the value for the ratio of propylene to ethylene for the first hydrocarbon feed and the second hydrocarbon feed predominantly comprising hydrocarbons having a maximum carbon number of 5.

2. The process as claimed in claim 1, characterized in that the second hydrocarbon is converted in the second cracking furnace (2) with cracking conditions that lead to a ratio of propylene to ethylene of up to 1.2 kg/kg, at the cracking furnace exit.

3. The process as claimed in claim 1, characterized in that the first hydrocarbon feed is converted in the first cracking furnace (1) with cracking conditions that lead to a ratio of propylene to ethylene of 0.3 to 0.75 kg/kg, more preferably of 0.4 to 0.65 kg/kg, at the cracking furnace exit.

4. The process as claimed in claim 1, in which the values for the ratio of propylene to ethylene for the first and second hydrocarbons differ by at least 0.1 kg/kg, preferably by at least 0.15 kg/kg, more preferably by at least 0.2 kg/kg.

5. The process as claimed in claim 1, characterized in that the second hydrocarbon feed consists for the most part of hydrocarbons having a carbon number of 5 or/and 4.

6. The process as claimed in claim 1, characterized in that the second cracking furnace is supplied with one or more recycled fractions (P, T) which are obtained from the product stream and which comprise predominantly hydrocarbons having a carbon number of not more than 5.

7. The process as claimed in claim 1, characterized in that the first cracking furnace is supplied with at least one fraction (U) which has been separated from the product stream and recycled, comprising predominantly hydrocarbons having a carbon number of at least 6.

8. The process as claimed in claim 1, characterized in that a fresh feed is used, which is fractionated into at least one first and one second fresh feed fraction, and the first fresh feed fraction is conducted at least partly into the first cracking furnace and the second fresh feed fraction at least partly into the second cracking furnace.

9. The process as claimed in claim 1, characterized in that the second cracking furnace (2) is supplied not only with the second fresh feed fraction (B2) but also with a further fresh feed (BL) consisting predominantly of hydrocarbons having a maximum carbon number of 5.

10. The process as claimed in claim 1, in which the cracking furnace exit temperature for the conversion in the second cracking furnace (2) is between 680° C. and 820° C., preferably between 700° C. and 800° C. and further preferably between 710° C. and 780° C. and more preferably between 720° C. and 760° C., and the cracking furnace exit temperature for the conversion in the first cracking furnace (1) is between 800° C. and 1000° C., preferably between 820° C. and 950° C. and more preferably between 840° C. and 900° C., the cracking furnace exit temperature of the first cracking furnace (1) being above that of the second cracking furnace (2).

11. The process as claimed in claim 10, in which the cracking furnace exit temperature for the conversion in the first cracking furnace (1) is at least 10° C. above, preferably at least 15° C. above, more preferably at least 20° C. above, the cracking furnace exit temperature for the conversion in the second cracking furnace (2).

12. The process as claimed in claim 1, in which 0.3 to 1.5 kg of steam per kg of hydrocarbon feed is used in the first cracking furnace (1), and 0.15 to 0.8 kg of steam per kg of hydrocarbon feed in the second cracking furnace (2).

13. The process as claimed in claim 1, in which at least one fraction (V) comprising predominantly hydrocarbons having a carbon number of 2 or 3 is obtained from the product stream and at least partly converted in a cracking furnace (3) for gaseous feed.

14. The process as claimed in claim 1, characterized in that the fresh feed (B) used for the first cracking furnace (1) or/and for the fresh feed for the fresh feed fractionation (7) comprises natural gas condensates and/or crude oil fractions, especially naphtha, and/or synthetic and/or biogenic hydrocarbons and/or mixtures derived therefrom.

* * * * *